United States Patent [19]

Siegel

[11] Patent Number: 4,855,087
[45] Date of Patent: Aug. 8, 1989

[54] PROCESS FOR THE PREPARATION OF 2-CHLOROETHANEPHOSPHONYL DICHLORIDE

[75] Inventor: Herbert Siegel, Hofheim am Taunus, Fed. Rep. of Germany

[73] Assignee: Hoechst Aktiengesellschaft, Frankfurt am Main, Fed. Rep. of Germany

[21] Appl. No.: 127,175

[22] Filed: Dec. 1, 1987

[30] Foreign Application Priority Data

Dec. 2, 1986 [DE] Fed. Rep. of Germany ....... 3641100

[51] Int. Cl.$^4$ ............................................. C07F 9/42
[52] U.S. Cl. ............................................. 562/817
[58] Field of Search ................................. 260/543 P

[56] References Cited

U.S. PATENT DOCUMENTS

| 3,183,264 | 5/1965 | Rochlitz et al. | 260/543 P |
| 3,574,735 | 4/1971 | Sennewald et al. | 260/543 P |
| 3,972,923 | 8/1976 | Finke et al. | 260/543 P |
| 4,213,922 | 7/1980 | Maier | 260/543 P |
| 4,735,748 | 4/1988 | Pieper | 260/543 P |

FOREIGN PATENT DOCUMENTS

| 0241115 | 10/1987 | European Pat. Off. ........ 260/543 P |
| 1568945 | 12/1966 | Fed. Rep. of Germany . |
| 2132962 | 1/1973 | Fed. Rep. of Germany . |
| 391699 | 9/1965 | Switzerland . |

Primary Examiner—Paul J. Killos

[57] ABSTRACT

The invention relates to a process for the preparation of 2-chloroethanephosphonyl dichloride by reaction of an ester of 2-chlorethanephosphonic acid of the formula

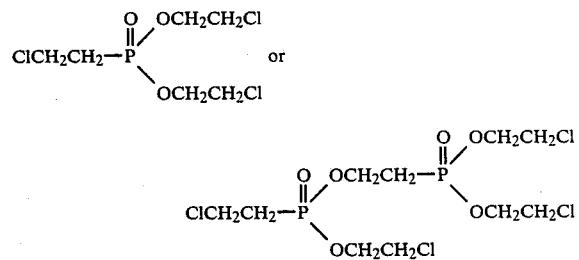

or a mixture of the two esters with thionyl chloride at a temperature of 60° to 160° C. Phosphine oxides are employed as catalysts therein. The thionyl chloride is added to the initially introduced ester.

6 Claims, No Drawings

PROCESS FOR THE PREPARATION OF 2-CHLOROETHANEPHOSPHONYL DICHLORIDE

The invention relates to a process for the preparation of 2-chloroethanephosphonyl dichloride by reaction of an ester of 2-chloroethanephosphonic acid of the formula

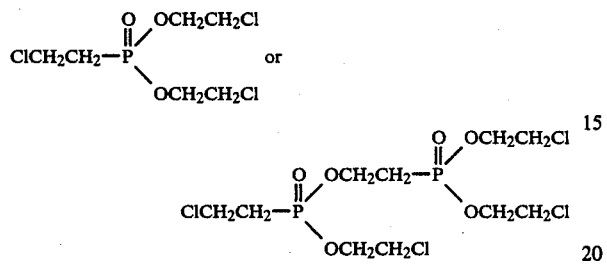

or a mixture of the two esters with thionyl chloride at a temperature of 60° to 160° C.

2-chloroethanephosphonyl dichloride

is a valuable intermediate. By hydrolysis 2-chloroethanephosphonic acid is obtained, which is important as a plant growth accelerator. By reaction with hydroxyalkyl or mercaptoalkyl compounds, phosphonates or thiophosphonates are obtained. Such compounds can be used as flameproofing agents or as plant protection agents. In addition, vinylphosphonyl dichloride can be prepared from 2-chloroethanephosphonyl dichloride by elimination of HCl (Swiss Pat. No. 391,699, German Offenlegungsschrift No. 1,568,945), which in turn can be hydrolyzed to vinylphosphonic acid. This is an important intermediate in the preparation of flameproofing agents. In addition it is an important monomer in the preparation of homopolymers or copolymers. Such polymers are important in paints, plastics, corrosion inhibitors and coating agents.

It is known from U.S. Pat. No. 4,213,922 that 2-chloroethanephosphonyl dichloride can be obtained from the abovementioned bis-2-chloroethyl 2-chloroethanephosphonate using thionyl chloride. In this process tertiary amines, N,N-disub-stituted formamides or N,N-disubstituted phosphoric triamides are employed as catalysts. However, in spite of long reaction times the yield is very low, as Example 4 of this literature reference shows.

The same reaction using phosgene instead of thionyl chloride is known from German Offenlegungsschrift No. 2,132,962. Phosphorus(V) compounds, such as triphenylphosphine oxide are among the catalysts employed here. These catalysts were already prior art on the priority date of U.S. Pat. No. 4,213,922; however, they are not used in processes according to the U.S. Patent. Thus it is obvious that, when thionyl chloride is used, the presence of phosphorus(V) compounds was not considered favorable.

Surprisingly, it has now been found that 2-chloroethanephosphonyl dichloride can be obtained in a short reaction time with high yields from the above esters of 2-chloroethanephosphonic acid using thionyl chloride in the presence of phosphine oxides, preferably in combination with alkali metal halides or alkaline earth metal halides. The same reaction, but using tertiary phosphines or alkali metal halides or alkaline earth metal halides, is described in German Patent Application No. P 36 29 579.5, which is not a prior publication.

The invention therefore relates to a process for the preparation of 2-chloroethanephosphonyl dichloride by reaction of an ester of 2-chloroethanephosphonic acid of the formula

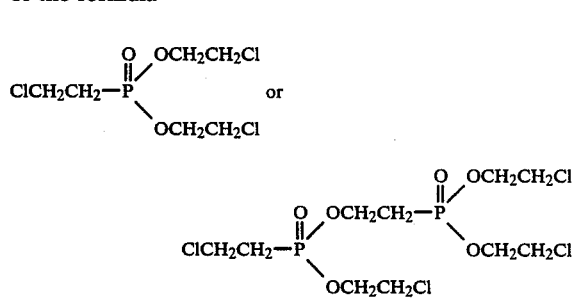

or a mixture of the two esters with thionyl chloride at a temperature of 60° to 160° C., which comprises carrying out the reaction in the presence of a catalyst which contains phosphine oxides of the general formula

in which the radicals $R^1$, $R^2$ and $R^3$ can be identical or different and denote straight-chain or branched $C_1$–$C_{10}$-alkyl, phenyl, or phenyl which is substituted with halogen radicals, $C_1$–$C_4$-alkyl radicals or $C_1$–$C_4$-alkoxy radicals.

The catalyst preferably also contains alkali metal halides or alkaline earth metal halides, in particular lithium bromide, in addition to the phosphine oxides.

$R^1$, $R^2$ and $R^3$ are preferably $C_1$–$C_4$-alkyl radicals, phenyl radicals or phenyl radicals substituted in the manner abovementioned.

The reaction temperature is 60°–160° C., preferably 60°–140° C., in particular 80°–130° C.

The molar ratio of thionyl chloride to the ester employed is 2:1 to 4:1, preferably 2.5:1 to 3.5:1.

The amount of catalyst is 0.1 to 10 mol percent, preferably 0.5 to 4 mol percent, based on the ester employed.

The following phosphine oxides are particularly suitable: triphenylphosphine oxide, tris(4-fluorophenyl)phosphine oxide, tris(4-tolyl)phosphine oxide, tris(4-methoxy-phenyl)phosphine oxide, (N,N-diethyl)aminomethyldiphenyl-phosphine oxide, tri-n-butylphosphine oxide, bis(4-methoxyphenyl)methylphosphine oxide. Triphenylphosphine oxide is especially suitable, above all combined with lithium bromide in a molar ratio of 10:1 to 1:10, preferably 1:1 to 1:5 ($Ph_3PO:LiBr$). The two components act in cooperation. It is thereby possible to reduce the temperature or to shorten the reaction time compared with the separate use of triphenylphosphine oxide.

The thionyl chloride is preferably added to the initially introduced ester in order to guarantee sufficient reaction time for the phosphonic acid ester, which is relatively slow to react. It is particularly preferred to introduce the thionyl chloride at the bottom of the reaction vessel into the initially introduced ester.

The dichloroethane, which is eliminated during the reaction, distils off at the reaction temperatures set and carries thionyl chloride out of the reaction vessel with increasing conversion, is preferably condensed and recycled. The unreacted thionyl chloride is optimally utilized by virtue of the circulation thus effected.

The reaction can also be carried out in the presence of an inert solvent. Chlorobenzene, dichlorobenzene or hydrocarbons may be mentioned as examples. Even in this case, the reaction is preferably carried out at 80° to 130° C.

The end of the reaction can be detected in that the evolution of SO$_2$ and HCl ceases.

For working up the reaction mixture the resulting chloroethane and, if appropriate, the unreacted thionyl chloride are removed by distillation. The 2-chloroethanephosphonyl dichloride formed can be purified by distillation.

The following examples serve to illustrate the invention. Crude bis-2-chloroethyl 2-chloroethanephosphonate, as obtained in the Arbusow rearrangement of tris-2-chloroethyl phosphite P(OCH$_2$CH$_2$Cl)$_3$ (German Offenlegungsschrift No. 2,132,962; Houben-Weyl, Volume XII/1 (1963), page 389) by heating at 140° C., was used as starting material. The crude ester consisted to about 55% of bis-2-chloroethyl 2-chloroethanephosphate

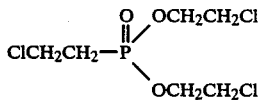

and about 38% of mono-2-chloroethyl-mono(bis-2-chloroethyl 2-chloroethanephosphonate) 2-chloroethanephosphonate

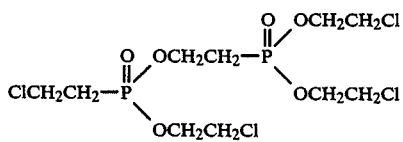

All batches and yields were based on a pure content of 93%.

EXAMPLE 1

150 g of crude bis-chloroethyl 2-chloroethanephosphonate and 149.1 g (1.25 mol) of thionyl chloride were heated within 30 minutes to 130° C. in the presence of 1.1 g of triphenylphosphine oxide. Eliminated dichloroethane and unreacted thionyl chloride distilled through a column into a receiver and were recycled into the reaction mixture through a dip tube at the bottom of the reaction vessel. The reaction mixture was heated for an additional 5.5 hours with continuous recycling of unreacted thionyl chloride and the highly volatile constituents were then removed from the reaction mixture by distillation, initially at atmospheric pressure and then at 150–250 mbar and 50°–70° C. 107.4 g of distillate were obtained, which still contained 20.6% of unreacted thionyl chloride, 81.5 g (84% of theory) of colorless liquid were than obtained at 4–5 mbar and 42°–83° C. as the main fraction, which consisted to 90 weight % of 2-chloroethanephosphonyl dichloride and to 10 weight % of vinylphosphonyl dichloride.

EXAMPLE 2

Analogously to Example 1, 150 g of crude bis-chloroethyl 2-chloroethanephosphonate and 149.1 g (1.25 mol) of thionyl chloride were heated within 30 minutes to 100° C. in the presence of 0.99 g (11.4 mmol) of LiBr and 1.1 g (3.96 mmol) of triphenylphosphine oxide, and the reaction mixture was held at this temperature of 5.5 hours. The mixture of thionyl chloride and dichloroethane removed by distillation was continuously recirculated through a dip tube at the bottom of the reaction vessel during this period. On distillation work-up, as described in Example 1, 104.0 g of an initial fraction, which consisted of 79.8 g of dichloroethane and 24.2 g of thionyl chloride, were obtained. 78.5 g (80% of theory) of 2-chloroethanephosphonyl dichloride and vinylphosphonyl dichloride in a weight ratio of 97:3 passed over as the main fraction.

EXAMPLE 3

Analogously to Example 2, 150 g of crude bis-chloroethyl 2-chloroethanophosphonate and 149.1 g (1.25 mol) of thionyl chloride were heated within 30 minutes at 100° C. in the presence of 2.12 g (7.35 mmol) of triphenylphosphine oxide. The reaction mixture was stirred for 5.5 hours at 100° C., and the mixture of thionyl chloride and dichloroethane removed by distillation was continuously recirculated through a dip tube at the bottom of the reaction vessel. Distillative work-up analogously to Example 2 gave 100.3 g of an initial fraction, which consisted of 66.6 g of dichloroethane and 33.7 g of thionyl chloride. 48.5 g (49% of theory) of 2-chloroethanephosphonyl dichloride and vinylphosphonyl dichloride in a weight ratio of 97:3 passed over as the main fraction.

I claim:

1. A process for the preparation of 2-chloroethanephosphonyl dichloride by reaction of an ester of 2-chloroethanephosphonic acid of the formula

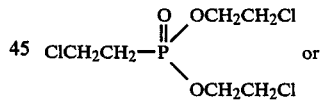 or

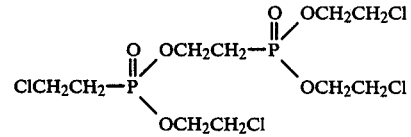

or mixture of the two esters with thionyl chloride at a temperature of 60° to 160° C., which comprises carrying out the reaction in the presence of a catalyst which comprises alkali metal halide or alkaline earth metal halide and phosphine oxides of the formula

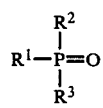

in which the radicals R$^1$, R$^2$ and R$^3$ can be identical or different and denote straight-chain or branched C$_1$-C$_{10}$-alkyl, phenyl, or phenyl which is substituted with halogen radicals, $C_1$–$C_4$-alkyl radicals or $C_1$–$C_4$-alkoxy radicals.

2. The process as claimed in claim 1, wherein a catalyst is employed which also contains lithium bromide in addition to the phosphine oxides.

3. The process as claimed in claim 1, wherein triphenylphosphine oxide or a combination of triphenylphosphine oxide with lithium bromide is employed as the catalyst.

4. The process as claimed in claim 1, wherein the dichloroethane which is eliminated and removed by distillation during the reaction is condensed and recycled.

5. The process as claimed in claim 1, wherein the thionyl chloride is added to the initially introduced ester.

6. The process as claimed in claim 1, wherein the thionyl chloride is added at the bottom of the reaction vessel to the initially introduced ester.

* * * * *